United States Patent [19]

Skold et al.

[11] Patent Number: 4,727,022
[45] Date of Patent: Feb. 23, 1988

[54] METHODS FOR MODULATING LIGAND-RECEPTOR INTERACTIONS AND THEIR APPLICATION

[75] Inventors: Carl Skold, Mountain View; Dennis R. Gould, San Gregorio; Edwin F. Ullman, Atherton, all of Calif.

[73] Assignee: Syntex (U.S.A.) Inc., Palo Alto, Calif.

[21] Appl. No.: 589,428

[22] Filed: Mar. 14, 1984

[51] Int. Cl.$^4$ .............. G01N 33/535; G01N 33/542; G01N 33/563; C12N 9/96; C12N 9/99
[52] U.S. Cl. .......................................... 435/7; 435/184; 435/188; 435/810; 436/512; 436/537; 436/808; 436/501
[58] Field of Search ............ 435/7, 26, 810, 184, 435/188; 436/512, 513, 548, 537, 808, 810, 815, 817, 501, 827, 537

[56] References Cited

U.S. PATENT DOCUMENTS

| | | | |
|---|---|---|---|
| 3,879,262 | 4/1975 | Schuurs et al. | 436/533 X |
| 4,130,462 | 12/1978 | Rubenstein et al. | 435/7 |
| 4,134,792 | 1/1979 | Boguslaski et al. | 435/7 X |
| 4,208,479 | 6/1980 | Zuk et al. | 435/7 |

Primary Examiner—Esther M. Kepplinger
Attorney, Agent, or Firm—Theodore J. Leitereg; Bertram A. Rowland

[57] ABSTRACT

Methods are provided for modulating Ligand-Receptor interactions by binding of molecules at two epitopes of a receptor, where the epitopes are in relatively close special relationship. By providing for inhibition of changes in conformation of the receptor, where the inhibition is due to steric interactions or molecular bridging between the two epitopic sites, Ligand-Receptor interactions may be modulated. The modulation of Ligand-Receptor interactions has application to diagnostic assays, modulation of cellular activity, and modulation of the physiological activity of macromolecular compounds.

16 Claims, No Drawings

METHODS FOR MODULATING LIGAND-RECEPTOR INTERACTIONS AND THEIR APPLICATION

BACKGROUND OF THE INVENTION

A. Field of the Invention

Many physiological processes involve the binding or complexation of two molecules which have a specific affinity. For the most part, one of the molecules will be a macromolecular protein. Upon binding of the macromolecular protein to its complementary binding member, the macromolecular protein will frequently undergo a change in conformation. In many physiological processes, this change in conformation serves as a signal for initiation of a physiological process. For example, receptors on cell surfaces act in this manner. The receptors bind to a complementary binding substance and undergo a change in conformation, which may change the characteristics or activity of the receptor or may signal the initiation of some process in the cell or both. In cases of enzymes, binding of the substrate to the enzyme frequently results in a change in conformation of the enzyme, which is essential for the enzymatic catalysis.

Receptors, such as membrane surface receptors and enzymes, find broad applications in a variety of environments. The ability to modulate the interaction between ligands and receptors can be employed in a variety of environments to modulate cellular function, to develop diagnostic assays, and to modulate physiological activity of macromolecular compounds.

B. Description of the Prior Art

Ngo & Lanhoff, FEBS Letters (1980) 116:285–288 describes the use of an enzyme modulator in homogenous enzyme immunoassays. See also U.S. Pat. No. 4,134,792.

SUMMARY OF THE INVENTION

Methods and compositions are provided for modulating receptor response. The receptor is characterized by having a pair of proximate determinant sites which are related in that a change in spacial relationship of the sites relative to each other is related to the interaction of the homologous ligand with its receptor. Site-directed binding molecules ("SDBM") are provided which bind to a related pair of sites on the receptor molecule surface. Binding of an SDBM to an individual site results in substantially less modulation than binding of the pair of sites in a manner which limits the conformational flexibility of the receptor. Bulking of the binding molecules or bridging of the binding molecules substantially modifies the reacting capability of the receptor molecule with ligand.

The modulation system is exemplified by a multiunit enzyme. Bridging of two specific epitopic sites by an antibody or two Fab fragments linked by a bridging member or bulked with antibodies to the Fab fragment substantially changes the enzymatic activity.

DESCRIPTION OF THE SPECIFIC EMBODIMENTS

Methods and compositions are provided for modulating the formation and chemistry of complexes between ligands and their homologous receptors. The method involves binding of site-directed binding molecule(s) ("SDBM") to two specific sites on the receptor surface. The sites are characterized in that individual binding of the SDBM's at a single site on the receptor, even when bulked as described subsequently, allows for a significant effect on the complexation and disassociation of the ligand and receptor, when both sites are bound. When both sites are occupied by the SDBM's and the SDBM's bridge the sites or are bulked, there is a substantial change in the equilibrium and/or rate of complex formation or disassociation of the complex and/or chemical transformation of the ligand.

The ability to modulate the interaction or reaction between a ligand and its homologous receptor can be applied in a variety of ways. For example, the rate of an enzyme catalyzed reaction can be modulated. Thus, in extracellular processes, the rate of enzyme reaction may be changed to affect a particular physiological function. Enzymes find application as labels in a wide variety of assays. By appropriate choice of binding members, one can provide for a modulation of the enzymatic activity in relation to a particular analyte. In many cellular processes, surface membranes mediate the initiation or level of the process. The ability to change the interaction of the homologous ligand with the surface membrane receptor will act to modulate the particular physiological function.

The subject invention therefore acts to modulate the interaction between a ligand and its homologous receptor. The interaction may be one of (1) simply binding, as in antigen-antibody complex formation; or (2) undergoing a reaction involving a chemical transformation, as in an enzyme-substrate binding, or (3) changing of conformation resulting in a change in a physiological activity, such as with surface membrane receptors and their reciprocal ligands. Therefore, the receptors which are modulated include a wide variety of proteinaceous substances, such as naturally occurring receptors, particularly surface membrane receptors, enzymes, antibodies, and lectins.

The receptor will be one or a complex of several proteinaceous macromolecules, which generally are at least about 15,000 molecular weight, more usually at least about 20,000 molecular weight and the large majority of which will be 30,000 molecular weight or greater. Usually, the molecules will be under 1,000,000 molecular weight, more usually under about 600,000 molecular weight and may exist as monomers or may be assemblies of up to 50 macromolecules (e.g., a ribosome). The receptor will be further characterized by having two sites in juxtaposition, such that when the sites are restricted in their relative movement to each other, there is a substantial change in the interaction of the receptor with its homologous ligand. The nature of the interaction will be discussed subsequently.

The surface membrane receptors may be varied widely in accordance with the function to be modulated. Surface membrane receptors include receptors involved with ion transport, opiate binding sites, steroid binding sites, Fc binding sites, histocompatibility antigens, viral recognition antigens, or the like.

The enzymes may be mono-subunit or multi-subunit enzymes, where the units may be the same or different. A wide variety of enzymes may be involved, such as hydrolases, e.g. glycosidases, esterases, etc.; oxidoreductases, e.g. dehydrogenases, oxidases, peroxidases, etc.; lyases; transferases; isomerases. For a more extensive list see U.S. Pat. No. 4,287,300, Table 1, bridging columns 16 to 19, which is incorporated herein by reference, Antibodies may include a complete antibody or fragment thereof, which antibodies include the various classes and types, such as IgA, IgD, IgE, IgG 1,2a, 2b and 3, and IgM. Fragments thereof may include Fab, Fv and F(ab')$_2$.

The ligand may be any ion molecule, organic or inorganic which binds to a receptor. The ligand will generally be at least about 7 atoms or molecular weight, e.g. Li, for an organic compound usually at least about 125, and may be 1,000,000 or more molecular weight, being haptenic or antigenic, binding to the receptor and dissociating in either the same or different form. The affinity may vary widely, generally having a K of association of at least about $10^5$. The degree of specificity or cross reactivity will vary widely, depending upon the nature of the ligand and its homologous receptor.

Where enzymes and substrates are involved as the receptor and homologous ligand, particularly for use in immunoassays, the ligand will frequently be a substrate which upon enzyme catalyzed reaction results in the formation or destruction of a molecule which provides a detectable signal. That is, the reaction will normally involve the formation or destruction of a chromophore, fluorescer or chemiluminescer. Various substrates have been published in the literature; for example, see U.S. Pat. No. 4,287,300. Other reactions of interest, which are not commonly employed, result in changes in pH, temperature, particulate formation, or the like. Of particular interest is the formation of a chromophore or fluorophore. A large number of enzymes are available which provide, directly or indirectly, for production of a detectable signal.

While preferably, a single enzyme will usually be involved, an enzyme cascade can also be employed, where the enzymes are related by the substrate of one enzyme being the product of the next enzyme. In some instances, this can provide for substantial amplification. By modulating the first enzyme in the series, one can modulate the amplified production of a product providing a detectable signal.

The site directed binding molecules are monoclonal antibodies or fragments thereof. Therefore, the monoclonal antibodies may be monovalent or polyvalent. The monoclonal antibodies will be specific for two sites, which sites may be identical or different. Where two sites are identical and are in relatively close juxtaposition, and inhibition of the relative movement of the sites affects the interacting (association, catalytic, disassociation, etc.) properties of the receptor, then either one two-site directed or two one site-directed binding molecules may be employed. For example, by employing multivalent IgG or IgM, the IgG or IgM may bridge the two sites, substantially locking them into a particular spacial relationship. Alternatively, if a single antibody is unable to bridge the two sites, because the two sites are too distant from each other or are different, non-bridging, e.g. monovalent, antibody fragments may be employed such as Fab, Fab', or Fv in conjunction with additional binding molecules.

Non-bridging site directed binding molecules may be modified for a variety of purposes. In assays for analytes, the monovalent SDBM's may be lightly conjugated with the analyte or an analog of the analyte of interest. The analyte may then serve as a site for specific binding molecules, which are bridging or bulking molecules, which binding molecules serve to substantially lock the two SDBM's in a particular conformation. This results in the receptor to which the SDBM's is bound being inhibited in its movement.

The analytes may include a wide variety of types of molecules, to which reciprocal specific binding molecules would bind, such as drugs, polynucleotides (particularly oligonucleotides), hormones, oligopeptides, proteins, factors, sugars, polysaccharides, antibiotics, or the like. For the most part these molecules will be less than about 10,000 molecular weight, more usually less than about 5,000 molecular weight, usually ranging from about 125 to 2,000 daltons.

Large molecules e.g. proteins and polynucleotides, of greater than about 10 kdal (kilodaltons) may be employed as analytes where change in enzyme activity will usually be obtained by bridging or bulking with antibody or antibody fragments. Even if the presence of the analyte bound to the SDBM results in a reduction in enzymatic activity, the subject invention will still be useful where a measurable further reduction is achievable. The degree of further reduction required will be dependent on a number of factors, such as the sensitivity with which enzyme activity can be measured, whether the assay is qualitative or quantitative, the amount of residual enzyme activity which can be modulated by bridging or bulking, and the like.

The bridging member serves to hold the SDBM's bound to the receptor in a particular conformation. Therefore, the bridging member will be related to the particular molecule conjugated to the non-bridging SDBM. The bridging member will be polyvalent, since it must bind to two molecules conjugated to two different SDBM's. Where the analyte is monovalent, two or more analyte molecules or analogs thereof may be joined together to provide the analyte in polyvalent form. For the most part, the bridging member will be a polyvalent receptor, such as naturally occurring receptors, e.g., avidin, which binds to biotin, an antibody, which can be directed to any hapten, Clq, or a polynucleotide, which homoduplexes at its termini with oligonucleotides conjugated to the SDBM. The oligonucleotide conjugates may be the same or different.

Instead of a bridging member, a bulky member may be employed, which can be the same as the molecules described for the bridging member or may be monovalent molecules. For the most part, these molecules will be at least about 30,000 molecular weight and may be 40,000 molecular weight or higher. The important factor is that they provide for sufficient bulk about the SDBM, so that the motion of the two SDBM's bound to the receptor is sterically constrained.

It is not necessary that both monovalent SDBM's be conjugated with analyte or analyte analog. In many instances it may be sufficient that only one SDBM is conjugated and the other SDBM is unconjugated to obtain a sufficient steric effect on bulking, so as to obtain an observable change in enzymatic activity. However, since using only one conjugated SDBM will usually provide for less change in enzymatic activity, both SDBM's will usually be conjugated with analytes.

The subject method is predicated upon the ability to find two adjacent sites on a molecule to which one or two SDBM's bind resulting in modification of the interaction of the receptor with its ligand. The SDBM's as already indicated are monoclonal antibodies. With those receptor molecules which have two adjacent sites which bind to the same SDBM, a single multivalent SDBM or two monovalent SDBM's may be used for modulation of receptor interaction with its ligand. This can occur where there is a plane of symmetry, particularly where a multi-subunit receptor molecule is involved, where two of the subunits are the same. Thus, on either side of the plane there will be sites which bind to the same SDBM.

Alternatively, one can prepare monoclonal antibodies to a receptor and select the monoclonal antibodies which individually as monovalent SDBM's do not significantly modulate the binding activity of the receptor when bound to the receptor, but upon bridging or bulking result in a substantial change in the interaction between the receptor and its homologous ligand. Thus, one screens a receptor of interest for the presence of such sites and may then use the receptor in accordance with the subject invention.

As already indicated, the subject invention can be used in assays for a wide variety of analytes, employing enzymes as the receptor and substrates as the ligand. By employing SDBM's to which are conjugated the analyte of interest or an analog thereof capable of competing with the analyte of interest for a specific binding molecule, usually an antibody, assays can be performed. The enzymatic activity can be related to the amount of analyte present in the assay medium.

A wide variety of mono- and polyepitopic analytes are described in U.S. Pat. No. 4,160,645, Columns 6 to 13, which description is incorporated herein by reference. The assay for the analyte will normally be carried out in an aqueous buffered medium at a moderate pH, generally close to providing optimum assay sensitivity. The assay can be performed without separation of any of the assay components or products.

The aqueous medium may be solely water or may include from 0 to 40 volume percent of a cosolvent. The pH for the medium will usually be in the range of about 4 to 11, more usually in the range of about 5 to 10, and preferably in the range of about 6.5 to 9.5. The pH will usually be a compromise between optimum binding of site directing binding members and the specific binding members, bridging and bulking members, as contrasted with the pH optimum for the enzyme.

Various buffers may be used to achieve the desired pH and maintain the pH during the determination. Illustrative buffers include borate, phosphate, carbonate, tris, barbital and the like. The particular buffer employed is not critical to this invention, but in an individual assay one or another buffer may be preferred.

Moderate temperatures are normally employed for carrying out the assay and usually constant temperatures during the period of the measurement, particularly for rate determinations. Incubation temperatures will normally range from about 5° to 45°, more usually from about 15° to 40° C. Temperatures during measurements will generally range from about 10° to 50°, more usually from about 15° to 40° C.

The concentration of analyte which may be assayed will generally vary from about $10^{-4}$ to $10^{-15}$M, more usually from about $10^{-6}$ to $10^{-14}$M. Considerations, such as whether the assay is qualitative, semiquantitative or quantitative, the particular detection technique and the concentration of the analyte of interest will normally determine the concentrations of the various reagents.

While the concentrations of the various reagents in the assay medium will generally be determined by the concentration range of interest of the analyte, the final concentration of each of the reagents will normally be determined empirically to optimize the sensitivity of the assay over the range. That is, a variation in concentration of the analyte which is of significance should provide an accurately measurable signal difference.

The optimization will usually involve combining the various reagents in the absence of the analyte to provide a low background value of enzymatic activity, generally less than 20% of the enzymatic activity in the absence of the other reagents, where modulation results in inhibition. Similarly, where modulation results in activation, one will usually have greater than about 70% of the maximum activity resulting from combination of the enzyme with the other reagents. In view of the diverse nature of the reagents, the difference in analytes, enzymes and detection systems, as well as the influences of the matrix of the sample, specific ratios of the various reagents cannot be provided.

While the order of addition may be varied widely, there will be certain preferences. The simplest order of addition is to add all the materials simultaneously and determine the change in enzymatic activity with time or the enzymatic activity when the mixture reaches a steady state.

Alternatively, one can combine the enzyme with the SDBM's to allow for binding of the SDBM's to the enzyme. More conveniently, an enzyme-SDBM reagent can be preprepared, which may be used directly. The sample and specific binding member for analyte ("antianalyte") may be combined initially. The SDBM-bound-enzyme may then be added and substrate for the enzyme added, either concomitantly with or subsequent to the addition of the SDBM-bound-enzyme. Optionally, an incubation step may be involved subsequent to each addition, generally ranging from about 30 seconds to 6 hours, more usually from about 2 minutes to 1 hour.

After all of the components of the assay have been combined, the enzymatic activity in the assay medium may be determined by means of the turnover rate. Depending upon the nature of the enzyme and the substrates, various techniques for detection may be employed. Conveniently, the determination can be colorimetric, generally at a wave length in the range of about 300 to 700 nm. Fluorometric measurements will generally be in the range of about 350 to 700 nm, more usually in the range of about 400 to 650 nm. For quantitation, assay media are prepared which have known amounts of analyte. By varying the amount of analyte in the assay media, one can develop standard curves to relate a particular enzymatic activity to an analyte concentration.

Compositions can be provided which can be used in the assay or kits can be provided having compositions in relative amounts to substantially optimize the accuracy and sensitivity of the assay.

As compositions, enzyme-SDBM-complexes employing monovalent SDBM's (Fab, Fab', Fv, etc.) can be provided. These compositions may be illustrated by way of formula as follows:

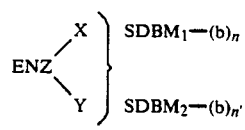

where
ENZ is an enzyme;

X and Y designate two epitopic sites on the enzyme, which sites may have the same or different binding characteristics, which are characterized by the movement of the sites relative to each other affecting the enzyme activity;

$SDBM_1$ and $SDBM_2$ are the same or different and are non-bridging binding molecules which specifically bind to X and Y respectively;

b is an analyte or analyte analog; and n and n' are the same or different and are on the average in the range of about 0 to 10, but at least one of n and n' is equal to or greater than 1.

Exemplary of a composition having the above formula is as follows: ENZ is glucose-6-phosphate dehydrogenase, $SDBM_1$ and $SDBM_2$ are Fab fragments, b is a drug, such as an antibiotic, opiate, steroid, or the like and n and n' are on the average in the range of 1 to 3 particularly, 1 to 2.

The kits can comprise the pre-prepared enzyme-SDBM-complex, substrate for the enzyme, a specific binding member, normally an antibody when a hapten or antigen is the analyte, and any additional materials, such as buffers, stabilizers, antioxidants, protein, e.g., serum albumin, or the like.

The following examples are offered by way of illustration and not by way of limitation.

EXPERIMENTAL

All of the temperatures not otherwise indicated are in centigrade. All parts and percents not otherwise indicated are by weight, except for mixtures of liquids which are by volume.

EXAMPLE 1

Preparation of mouse monoclonal antibodies to glucose-6-phosphate dehydrogenase (G6PDH).

Ascites fluid was purified as follows: Protein (2 ml) was precipitated with about 50% saturated ammonium sulfate and then twice with 40% saturated ammonium sulfate. The protein was isolated and dialyzed against 10 mM phosphate buffer, resulting in some precipitate. The precipitate was resuspended in about 1 ml of 50 mM tris-500 mM NaCl buffer. Absorption ($A_{280}$) at 1:20 dilution was 0.65 (using $\epsilon = 1.5$) indicating 8.7 mg/ml.

The antibody was characterized as $IgG_{2b}$.

The antibody was shown to inhibit G6PDH in the following manner. Various dilutions of the antibody were prepared. The enzyme solution was 2.44 µg/ml (about $2.2 \times 10^{-8}M$). Three different protocols were tested In the first protocol, 50 µl of enzyme and 50 µl of the antibody dilution were mixed, incubated for 20 min., then diluted with 500 µl of tris-rabbit serum albumin (RSA) buffer and assayed by the addition of 50 µl of the substrate solution plus 250 µl of the buffer. The second protocol added 50 µl of the antibody dilution to a solution of 50 µl of the enzyme solution in 500 µl of the buffer, followed by 20 minutes incubation, followed by the addition of 50 µl of substrate and 250 µl of buffer. The third protocol involved combining 50 µl of each solution in 250 µl of buffer seriatim in the order of enzyme, antibody and substrate.

In each case, the sample was then introduced into the instrument and maintained at 37°, and the first reading taken at 10 seconds and the second reading taken at 40 seconds at 340 nm and the rate reported as 2.66 times the observed absorbance change. The following table indicates the results.

TABLE 1

| Ab dilution | Protocol I | Protocol II | Protocol III |
|---|---|---|---|
| | | Rate (ΔA) | |
| 1:200 | — | 883 | 161 |
| 1:280 | 921 | 814 | 155 |
| 1:400 | 881 | 736 | 149 |
| 1:560 | 838 | 669 | 156 |
| 1:800 | 800 | 564 | 203 |
| 1:1120 | | 394 | 329 |
| 1:1600 | 542 | 326 | 502 |
| 1:2240 | 721 | 606 | 653 |
| 1:3200 | 841 | 805 | 795 |
| 1:4480 | 919 | 924 | 895 |
| 1:6400 | 965 | 984 | 953 |

EXAMPLE 2

Preparation of anti-G6PDH Fab.

To 0.5 ml of mouse anti-G6PDH, which had been purified by conventional techniques, and had an estimated concentration of 9 mg/ml was added 50 µl of 10×PBS. To this solution was added 50 µl of a papain solution (1 mg/1 ml) in 100 mM cysteine, 20 mM EDTA and 100 mM sodium phosphate, at pH 7.3 and the mixture incubated at 37° for one hour. Gel electrophoresis indicated the reaction was complete. The digest was dialyzed against 10 mM tris, pH 8, 5 mM sodium azide. The preparation was then passed over a protein A column with the eluate being about 0.5 mg/ml protein by UV ($A_{280}$=about 0.7). The Fab product provided a distinct band different from the parent antibody on gel electrophoresis.

To demonstrate the effect of binding of the mouse anti-G6PDH Fab followed by the binding of rabbit anti-mouse IgG, the following protocol was employed. To 50 µl of G6PDH 3.2 µg/ml was added 200 µl of buffer followed by 50 µl of 1:100 dilution anti-G6PDH Fab plus 200 µl of buffer. To this mixture was then added 50 µl of rabbit anti-mouse IgG plus 200 µl of buffer and the mixture incubated for 45 seconds. After adding 50 µl of substrate and 200 µl of buffer, the solution was mixed and read at 37° after 15 seconds and the second reading at 45 seconds at 340 nm, and the difference×2.66 reported as rate. The following table indicates the results.

TABLE 2

| Dilution of Rabbit anti-mouse IgG | Rate ΔA |
|---|---|
| 1:1 | 589 |
| 1:2 | 691 |
| 1:4 | 790 |
| 1:8 | 861 |
| 1:16 | 947 |
| 1:32 | 1009 |
| 1:64 | 1055 |
| 1:128 | 1070 |
| 1:256 | 1077 |
| ∞ | 1083 |
| control* | 940 |

*no Fab present

EXAMPLE 3

Preparation of digoxin conjugate of Fab anti-G6PDH.

Into a reaction flask was introduced 17 mg of the O-carboxymethyl oxime of 3-ketodigoxigenin, 250 µl of a 21 mg/ml solution of N-hydroxy succinimide in DMF and about 7.5 mg of EDCI (ethyl dimethylaminopropyl carbodiimide) and the mixture stored overnight at room temperature. The next morning an additional 5.85 mg of EDCI was added (50 μl of 117 mg EDCI/100 ml of DMF) and after 3 hours the reaction was shown to be complete by TLC. The N-hydroxy succinimide ester prepared above was diluted with DMF (25 μl and 150 μl DMF) and was added to 100 μl of purified Fab anti-G6PDH and 20 μl of DMF in 1 μl and 3 μl portions in separate reaction vessels. After about 0.5 hour, the reaction mixture was chromatographed on G-25 Sephadex. The products are referred to as "1" and "3" conjugates.

Both of the above products were shown to provide for reduced rates of G6PDH upon addition of anti-digoxin as compared to carrying out the assay in the absence of anti-digoxin. The protocol involved combining 50 μl of G6PDH plus 250 μl of buffer to which is added 50 μl of the conjugate of digoxin and Fab in 250 μl of buffer. The solution is mixed and 50 μl of 1:100 anti-digoxin and substrate or substrate only plus 250 μl of buffer is added. The rate is determined as previously described.

TABLE 3

| Fab dilution | Rate (ΔA) Conjugate | |
|---|---|---|
| | "1" | "3" |
| 1:5 | 1050 | 876 |
| 1:10 | 939 | 709 |
| 1:20 | 833 | 671 |
| 1:40 | 828 | 851 |
| 1:80 | 910 | 1001 |
| 1:160 | 1030 | 1064 |
| 1:320 | 1080 | 1095 |
| 1:640 | 1094 | 1105 |
| ∞ | 1103 | 1101 |

It is evident from the above results, that the subject invention provides for the modulation of enzyme activity in relation to the amount of analyte in the medium. The method does not require the covalent modification of an enzyme, since the method employs the natural enzyme. Further, one can provide the enzyme as a reagent that is bound to a Fab fragment to avoid an addition during the assay.

Using an assay system similar to that described above, the effect of various dilutions of anti-digoxin on digoxin-Fab-G6PDH complexes was determined.

| Dilution of Anti-digoxin | 1:40 Dilution of "1" plus enzyme Rate | 1:20 Dilution of "3" plus enzyme Rate |
|---|---|---|
| 1:100 | 844 | 680 |
| :200 | 921 | 815 |
| :400 | 1018 | 969 |
| :800 | 1099 | 1078 |
| :1000 | 1151 | 1132 |
| :3200 | 1183 | 1161 |
| :6400 | 1184 | 1178 |
| :∞ | 1197 | 1183 |

EXAMPLE 4

Preparation and Use of Digoxin Conjugate of Fab' Anti-G6PDH

I. Bromoacetyl derivative of digoxin.

3-Ketodigoxigenin O-carboxymethyloxime (131 mg), DCC (82 mg) and N-hydroxysuccinimide (51 mg) were dissolved in 1.0 ml DMF and stored overnight. The crude solution of NHS ester was filtered and then treated with 0.5 ml of ethylenediamine. The resulting solution was evaporated, taken up in aqueous phosphate buffer (9 ml) and treated with 0.3M bromoacetic acid NHS ester (4 ml). The resulting bromoacetyl derivative was purified by preparative TLC, and then dissolved in 50% aqueous methanol to give a solution approximately 0.1M in "bromoacetyl digoxin."

II. Digoxin conjugate of Fab' fragment.

A monoclonal antibody of the same specificity as that described in Example 1, but of $IgG_{2a}$ subclass, was converted to $(Fab')_2$ fragments by treatment with pepsin. 50 μl of a solution of $(Fab')_2$ (1.5 mg/ml) was treated with 10 μl of 3 mM dithioerythritol in 50 mM tris, pH8. After 1 hour, the solution was treated with 3 μl of 0.1M "bromoacetyl digoxin." After storage overnight at 4°, the conjugate was purified by chromatography on Sephadex G-25.

III. Complex of Digoxin-labeled Fab' and G6PDH.

500 μl of a solution of digoxin-labeled Fab' and 3 μl of 4.1 mg/ml G6PDH were mixed to form a complex of labeled Fab' and enzyme. The complex was purified using DEAE-Biogel A in a batch procedure.

IV. Inhibition of Digoxin-labeled Fab'-G6PDH complex by anti-digoxin, and assay for digoxin.

50 μl of various dilutions of anti-digoxin antiserum, 50 μl of digoxin-labeled Fab'-G6PDH complex, and 50 μl of substrate were dispensed seriatim into 750 μl of 55 mM tris buffer, pH 8, which contained 1 mg/ml rabbit serum albumin. The resulting enzyme activity was measured as an absorbance change between 15s and 45s after introduction of the sample into the spectro-photometer, and is reported as 2.66×ΔmOD.

| Dilution of Anti-digoxin | Rate |
|---|---|
| 1:50 | 451 |
| :100 | 456 |
| :200 | 471 |
| :400 | 500 |
| :800 | 552 |
| :1600 | 606 |
| :3200 | 627 |
| :6400 | 646 |
| :12800 | 659 |
| :∞ | 663 |

A standard curve for digoxin was constructed by mixing 50 μl digoxin calibrator and 50 μl 1:1600 dilution of anti-digoxin in 400 μl tris-RSA buffer, incubating for 100s, adding 50 μl of the digoxin-labeled-Fab'-G6PDH complex and 50 μl of substrate in 400 μl buffer and assaying for enzyme activity. The rate reported is absorbance change between 15s and 115s and is reported as 2.66×ΔmOD.

| Digoxin Conc. in Calibrator | Rate |
|---|---|
| 0 mg/ml | 924 |
| 1 | 912 |
| 2 | 914 |
| 4 | 924 |
| 8 | 942 |
| 16 | 969 |
| 32 | 1013 |
| 64 | 1049 |
| 128 | 1067 |

EXAMPLE 5

Preparation of Murine Monoclonal Antibody to Glucose-6-phosphate Dehydrogenase ("G6PDH")

As antigen, either G6PDH-digoxin conjugate (see below for preparation) or native G6PDH (Worthington Enzymes Lot M11) can be employed or a combination, where successive inoculations are performed. Balb/c mice, females (Simonsen Labs) were inoculated according to the following schedule.

G6PDH-digoxin (100 μg) homogenized in complete Freund's adjuvant (0.2 ml) was injected interperitoneally, followed at two week intervals with booster inoculations; (2×) with 100 μg G6PDH-digoxin homogenized in incomplete Freund's adjuvant ("IFA") and (1×) with 100 μg G6PDH in IFA. After one week, the mice were bled and serum tested against the G6PDH-digoxin conjugate and native G6PDH by Ouchterlony immunodiffusion. Mice whose serum showed Ouchterlony precipitate bands were tolerized on the following schedule:

| Day of "Tolerization" | Immunogen Concentration in HBS*, μg | Site of Inoculation |
|---|---|---|
| 1 | 100 | subcutaneously several sites |
| 2 | 200 | |
| 3 | 200 | |
| 4 | 200 | intravenous (i.v.) |
| 5 | — | |
| 6 | — | |
| 7 | fused | |

*HBS - Hank's Balanced Salts

The myeloma cell NS-1 (P3-NS1-1)("HAT" selectable) was collected in log growth phase, $10^7$ cells washed and diluted into 20 ml of Dulbecco's Modified Eagle Medium ("DMEM"). Mouse spleens were aseptically removed, the spleen disrupted in a 7 ml glass bore tissue homogenizer and the cellular dispersion added directly to the NS1 cells. The cellular mixture was centrifuged, washed 3× DMEM and then resuspended in 2 ml of 38% (w/v) polyethylene glycol (PEG-1540) in DMEM. The suspension was then centrifuged at gradually increasing force 250 G, 2', 500 G, 2', 1000 G, 2'. The supernatant was carefully removed and the pellet gently resuspended in 6 ml DMEM supplemented with 15% fetal calf serum, 10% NCTC 109 (thymidine hypoxanthine supplement, Microbiological Assoc.), 0.2 u bovine insulin/ml, 0.45 mM pyruvate, 1 mM oxaloacetate, 2 mM L-glutamine and 50 mg/ml gentamicin ("Super DMEM"). Cells were centrifuged, the pellet washed once and resuspended in 200 ml "HAT" selective medium (Super DMEM, 0.1 mM hypoxanthine, 0.01 mM aminopterin, 0.016 mM thymidine). The suspension was plated into 10 96-well plates. The cells were fed with the "HAT" medium on day 7 and additional feedings on days 9 and 14 were made as required.

An ELISA assay was employed to screen the supernatants from hybridomas. Into each well (Costar EIA plate, 96 wells) is successively introduced and flicked out: 100 μg/ml G6PDH for 2 hours at 37° C.; 100 μl 1% fetal bovine serum in PBS for 1 hour at 37° C.; and 100 μl culture supernatant for 1 hour at 37° C. The plates are then washed 3× with PBS +0.05% Tween 20. Anti-mouse polyclonal antibody (100 μl, 1 μg/ml) conjugated to alkaline phosphatase is added and incubated for 1 hour at 37° C. and washed 3× with PBS-Tween 20. Finally, 100 μl of 0.6 mg/ml p-nitrophenyl phosphate in substrate buffer (0.098 g $MgCl_2.H_2O$, 192 ml ethanolamine; $H_2O$ to 2 L, pH 9.8). Optical densities (OD's) are read at 405 nm on a 96-well Titertek reader (Flow Labs).

One colony designated II-1H9 gave a reading of 0.440 after 20 minutes incubation. The antibody from this hydridoma was combined with G6PDH and was shown to provide a biphasic effect on G6PDH activity.

Subsequent fusions were repeated, immunizing with native G6PDH using CB6F1/J mice (Jackson Labs). Three colonies were found to provide antibodies which resulted in a biphasic effect on G6PDH.

These colonies were designated V8Cl12, V8G12 and V1A1 and the hybridoma V8Cl12 was deposited at the A.T.C.C. on Mar. 13, 1984 and given accession no. HB8498.

The digoxin-G6PDH conjugate is prepared as follows. Into a solution of 2.56 g 3-ketodigoxigenin and 3.3 g of sodium acetate is added 1.57 g carboxymethoxylamine hydrochloride with stirring and the mixture refluxed under $N_2$ for 2 hours. After concentration in vacuo, 320 ml of 5% aqueous $NaHCO_3$ is added and the aqueous solution extracted 3×200 ml $HCCl_3$. After acidifying the aqueous solution with 280 ml 1N HCl, the aqueous solution is extracted 10×125 ml ethyl acetate, the extracts combined and dried over anh. $MgSO_4$. The product is then isolated by filtration and evaporation yielding 2.59 g, which is further purified by dissolving in hot 7:10 methanol; ethyl acetate (60–80 ml). The product is precipitated from the cooled solution by the addition of pentane. After crystallization is complete, the product is isolated by filtration and dried in vacuo.

To 203.6 mg of the above dry product is added 2.2 ml DMF. After dissolution with stirring, 62 μl of triethylamine is added below the surface, the solution cooled to −15° to −20° C. and 82 μl of carbitol chloroformate added quickly below the surface. A precipitate forms and the mixture is continuously stirred while cold for 90 min. The supernatant is then used for conjugation.

To a solution of G6PDH (~6 mg/ml) in 3 ml Tris-buffer (0.055M Tris HCl, pH 8.0), was added with agitation 45 mg glucose-6-phosphate and 90 mg NADH, followed by the slow addition of 1.5 ml Carbitol while cooling the solution. The Carbitol is introduced below the surface, the addition requiring about 35–45 min. The pH is adjusted to 8.9, followed by the addition of 25 μl increments of the activated digoxin solution at a rate of 50 μl/min until a ratio of 0.4 mg/mg of digoxin/G6PDH is obtained. Digoxin addition is terminated and the enzyme conjugate is then chromatographed on a G50 Sephadex column equilibrated with Tris-HCl buffer plus preservatives (0.05% $NaN_3$, 0.005% Thimerosal) and 18–22 ml fractions collected and monitored. (Flow rate, ~6–10 ml/min). Enzyme conjugate containing fractions are pooled and stored in the cold.

The subject invention need not be used in diagnostic assays, but also can be used for the modulation of enzyme activity in vitro or in vivo. Thus, in studying cellular function one can selectively modulate the physiological activity of one or more surface membrane proteins, including enzymes.

Although the foregoing invention has been described in some detail by way of illustration and example for purposes of clarity of understanding, it will be obvious that certain changes and modifications may be practiced within the scope of the appended claims.

What is claimed is:

1. A method for modulating complex formation between a receptor and its homologous ligand,
said method comprising:
combining (a) a receptor having a pair of proximate determinant sites which have the same or different binding specificity and are related in that a change in spatial relationship of the pair of sites relative to each other is related to the interaction capability of said receptor with its homologous ligand, (b) site-directed binding molecules ("SDBM's") to said pair of determinant sites on said receptor, wherein said SDBM's specifically bind to and bridge said pair of determinant sites and affect the interaction of said receptor with said ligand, with the proviso that when said determinant sites in said pair are not both bound and bridged by a single SDBM, molecules binding specifically to and bridging said SDBM's are added to bind and bridge to said SDBM's, said binding of said SDBM's to and the bridging of said receptor determinant sites thereby modulating the ability of the receptor to bind to said ligand, and (c) said ligand.

2. A method according to claim 1, wherein a single SDBM binds to both determinant sites of said pair.

3. A method according to claim 2, wherein said receptor is an enzyme and said ligand is a substrate.

4. A method according to claim 1, wherein each determinant site is bound by an individual SDBM molecule.

5. A method according to claim 4, wherein said SDBM's are intact immunoglobulins and said molecules binding specifically to said SDBM's are polyvalent immunoglobulins specific for said SDBM's.

6. A method according to claim 4, wherein said SDBM's are antibodies, or fragments of said antibodies, said SDBM's being conjugated to analyte, or analog of analyte, and said molecules binding specifically to said SDBM's are polyvalent antibodies specific for said analyte.

7. A method according to claim 4, wherein said receptor is an enyzme and said ligand is a substrate.

8. A method for determining the presence of an analyte in a sample suspected of containing said analyte,
said method comprising:
combining in an aqueous assay medium
(a) a sample suspected of containing said analyte wherein said analyte is a specific binding pair member, said pair consisting of first and second binding members,
(b) an enzyme having a pair of proximate determinant sites, which have the same or different binding specificity and are related in that inhibition of movement of the pair of sites relative to each other modulates the interaction between said enzyme and its substrate,
(c) site-directed binding molecules ("SDBM's") which are molecules to which are conjugated an analog of said first binding member capable of binding to said second binding member and said SDBM's specifically bind to said pair of determinant sites, with the proviso that when said second binding member is monovalent, then said second binding member in polyvalent form is used separately or in combination with said enzyme,
(d) substrate for the enyzme, and
(e) additionally second binding member, when said analyte is first binding member; and
determining the enzyme activity in said assay medium as related to the enzyme activity of an assay medium having a known amount of analyte.

9. A method according to claim 8, wherein said analyte is a hapten of less than about 2,000 molecular weight.

10. A method according to claim 8, wherein said analyte is a polyvalent immunoglobulin.

11. A method according to claim 8, wherein said enzyme is glucose-6-phosphate dehydrogenase.

12. A method according to claim 11, wherein said SDBM's are monoclonal, monovalent immunoglobulin fragments.

13. An assay kit, comprising in packaged combination; (1) an enzyme characterized by having a pair of proximate determinant sites which have the same or different binding specificity and are related in that inhibition of movement of the pair of sites relative to each other modulates the interaction capability of said enzyme to its substrate; (2) site-directed binding molecules ("SDBM's") which bind specifically to said pair of determinant sites and to which are conjugated per SDBM at least one molecule capable of competing with a first binding member for a second binding member, wherein said first or second binding member is an analyte, the binding of said SDBM's to said determinant sites thereby modulating the ability of said enzyme to bind to its substrate.

14. An enzyme-site directed binding member-complex of the formula

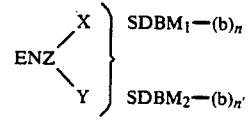

wherein:
ENZ is an enzyme;
X and Y designate two epitopic sites on the enzyme, which sites are the same or different, said sites being characterized by inhibition of movement of the sites relative to each other resulting in modulation of enzyme activity;
$SDBM_1$ and $SDBM_2$ are the same or different and are non-bridging binding molecules, which specifically bind to X and Y, respectively;
b is an analog of an analyte bound to said SDBM; and
n and n' are the same or different and are on the average in the range of 0 to 10, wherein at least one of n and n' is at least one.

15. A complex according to claim 14, wherein said $SDBM_1$ and $SDBM_2$ are the same Fab fragment and said ENZ is glucose-6-phosphate dehydrogenase.

16. The assay kit of claim 13 which further comprises said second binding member.

* * * * *